United States Patent [19]

D'Orazio

[11] 4,363,798

[45] Dec. 14, 1982

[54] TERMITE BAIT COMPOSITION

[75] Inventor: Vincent T. D'Orazio, Racine, Wis.

[73] Assignee: S. C. Johnson & Son, Inc., Racine, Wis.

[21] Appl. No.: 281,542

[22] Filed: Jul. 9, 1981

[51] Int. Cl.³ .................. A01N 25/00; A01N 59/14
[52] U.S. Cl. ............................. 424/84; 424/148; 424/DIG. 11
[58] Field of Search ............. 424/84, 148, DIG. 11

[56] References Cited

U.S. PATENT DOCUMENTS 3,070,495  12/1962  Esenther ........................ 424/84

FOREIGN PATENT DOCUMENTS

| 978853 | 6/1975 | Canada | 424/148 |
| 1682 | of 1876 | United Kingdom | 424/148 |
| 8602 | of 1892 | United Kingdom | 424/148 |
| 5705 | of 1896 | United Kingdom | 424/148 |
| 21567 | of 1908 | United Kingdom | 424/148 |

OTHER PUBLICATIONS

The Dispensatory of the U.S.A. (1947), published by J. B. Lippincott Co., Phil., pp. 164–167.

*Primary Examiner*—Donald B. Moyer

[57] ABSTRACT

Termite baits utilizing brown rot fungus as an attractant and utilizing boron compounds selected from colemanite, ulexite and calcium boride in mixtures effectively sufficient to kill termites without creating bait shyness.

10 Claims, No Drawings

TERMITE BAIT COMPOSITION

BACKGROUND OF THE INVENTION

This invention relates to termite baits and a method of using the same for termite control.

Each year, termites do substantial damage to structures and cause millions of dollars in economic loss. Termites, especially subterranean termites, feed on wood, and primarily by wood infected by fungus. In the early 1960's, it was found that the brown rot fungus, *lenzites trabea*, was especially attractive to subterranean termites. When this fungus was cultured on pine blocks, an effective termite attractant was prepared.

Even though methods of attracting termites have been known, the only successful termite bait/toxicant combination was a combination of this fungus with the insecticide Mirex, sold by Allied Chemical. Mirex, however, has been unavailable for use because of toxicology problems and, accordingly, a search has been conducted for an effective replacement for the Mirex in a termite bait composition.

Mirex was an especially attractive toxicant for termite baits because of its method of activity. This material was a relatively slow-acting toxicant which allowed the termite workers to injest the toxicant and communicate the source of the bait to other termite workers within the colony.

Due to the nature of termite colonies and the highly interrelated social order within the colony, the killing of substantial numbers of worker termites will sufficiently disrupt the colony structure so as to cause the colony to ultimately die off.

If the toxicant in the termite bait is too rapid acting, other termites will develop bait shyness and shy away from that particular bait material.

It has now been found that highly effective termite bait compositions can be prepared by mixing an effective amount of brown rot fungus, *lenzites trabea*, with from 0.1 to 20% by weight of a boron compound selected from the group consisting of calcium boride, colemanite, ulexite and mixtures thereof.

OBJECTS AND ADVANTAGES

It is, therefore, the primary object of the present invention to provide an improved termite-control bait composition.

It is a further object of the present invention to provide a method of controlling termites by placing these baits around an object to be protected.

It is a still further object of the present invention to provide a termite bait which uses, as a toxicant, a relatively innocuous, naturally occurring material as the active agent, so as to control termites without undue effect on the ecology.

Still further objects and advantages of the present invention will become more apparent from the following detailed description thereof.

DETAILED DESCRIPTION

The baits of the present invention comprise wood which has been innoculated with *lenzites trabea* and mixed with an appropriate amount of boron compound, i.e., from 0.1 to 20% by weight.

The preferred termite baits utilize wood which has been innoculated with the *lenzites trabea* fungus, which is then converted into sawdust. This sawdust is mixed with an equal amount of cellulosic binder, toxicant and water. This mixture is then blended together and dried.

As the improved toxicants for use in the present invention, a variety of boron compounds may be used. Suitable boron compounds include calcium boride ($CaB_6$), ulextile, a native California borate having the empirical formula $Na_2O.2CaO.5B_2O_3.16H_2O$ and colemanite, a native California borate having the empirical formula $2CaO.3B_2O_3.5H_2O$.

The base of the present invention should include from 0.1 to 20% by weight of boron compound. Within this range, it has been found that the termites injest a lethal dose on one visit to the bait, while the concentration of toxicant is not so high as to cause quick mortality creating bait shyness. It has been preferred that the boron compound be present in an amount from 1 to 10% by weight of boride compound. Furthermore, the preferred boron compound is ulexite.

The bait of the present invention can be compared in a variety of methods. One method includes innoculating wood blocks with brown rot fungus. These blocks can then be impregnated with the required toxicant. A preferred method, however, utilizes blocks which have been innoculated with the brown rot fungus and which are then ground into sawdust. This sawdust containing the brown rot fungus is then mixed with a suitable amount of cellulosic binder in a slurry and allowed to dry. At this time, the toxicant is also added to produce dry sheets of material which is attracting to termites. At the present time, it has been found that a particularly effective bait can be prepared which incorporates from 30 to 50% by weight of a sawdust containing the brown rot fungus, from 30 to 50% by weight of a cellulosic binder, and from 0.5 to 20% by weight of a boron containing toxicant.

Suitable cellulosic binders include various papers, including filter-type paper, wood pulp and the like. The paper or cellulosic binder merely serves as an extender for the sawdust and aids in holding this material together. The cellulosic binder is a diluent or extender which allows the use of less innoculated wood saw dust. The composition and methods of the present invention will now be illustrated by way of the following examples which are for the purposes of illustration and are in no way to be considered as limiting. In the following examples, all parts and percentages are by weight and all temperatures in degrees Centigrade, unless otherwise indicated.

EXAMPLE 1

A series of termite bait formulations are prepared by first innoculating blocks of wood with brown rot fungus and *lenzites trabea* and incubating this fungus for about 20 days. These blocks are then converted to sawdust. The sawdust is mixed with an equal weight of blotter paper and the amount of ulexite shown in Table I. Sufficient water is added to form a slurry of the sawdust paper mix. This mixture is then processed in a blender to a slurry and poured onto a screen. The resulting mat is dried and cut into $1'' \times 1'' \times \frac{1}{8}''$ squares for testing. The squares are placed in petri dishes and dampened with water for testing. Twenty termites were placed in these dishes and the mortality noted. This test was replicated five times. The number of termites which died was observed, as was the number of days to the first termite death. In addition to the baits containing a toxicant, a control was prepared in the same manner without any ulexite, as shown in Table I.

TABLE I

| Run | % Ulexite | Average Days to First Death | Average Days to 100% Dead |
|---|---|---|---|
| A (Control) | — | 49+* | 49+* |
| B | 0.1 | 12.0 | 23.4 |
| C | 0.5 | 11.0 | 23.8 |
| D | 1.0 | 10.2 | 19.0 |
| E | 5.0 | 4.2 | 16.0 |
| F | 10.0 | 4.2 | 14.8 |
| G | 20.0 | 4.2 | 12.8 |

*49+ - Test Terminated at 49 days. Only nominal mortality (7%).

As is apparent, a relatively small amount, 0.1% ulexite, is sufficient to create 100% termite mortality after 23 days. Furthermore, the time to first death is 12 days, which is close to a very desired level, since it has been found that if mortality begins earlier than 4 days, termites quickly develop bait shyness.

EXAMPLE 2

The procedure of EXAMPLE 1 was followed, with the exception that colemanite replaced the ulexite as the toxicant in the baits. The results are shown in Table II.

TABLE II

| Run | % Colemanite | Average Days to First Death | Average Days to 100% Dead |
|---|---|---|---|
| A | — | 49+ | 49+ |
| B | 0.1 | 24.2 | 42.5 |
| C | 0.5 | 14.8 | 30.8[1] |
| D | 1.0 | 14.0 | 23.8 |
| E | 5.0 | 6.6 | 21.0 |
| F | 10.0 | 5.2 | 19.8 |
| G | 20.0 | 5.0 | 15.0 |

[1]Average of 4 replicates. Other replicate did not have 100% mortality at termination of test.

As is apparent from the above data, colemanite is not quite as effective a toxicant as ulexite, although at substantial quantities, i.e., 0.5%, it does have good 100% mortality and an acceptable number of days to the first termite death.

EXAMPLE 3

The procedures of EXAMPLE 1 is repeated, with the exception that calcium boride replaces the ulexite as the toxicant. The results are shown in Table III.

TABLE III

| Run | % Calcium Boride | Average Days to First Death | Average Days to 100% Dead |
|---|---|---|---|
| A | — | 46+* | 46+ |
| B | 0.1 | 23.0 | 38.0 |
| C | 0.5 | 15.6 | 26.6 |
| D | 1.0 | 12.2 | 23.6 |
| E | 5.0 | 10.6 | 18.6 |
| F | 10.0 | 5.0 | 14.4 |
| G | 20.0 | 4.8 | 12.0 |

*46+ - Test terminated at 46 days. Only nominal (7%) mortality.

As is apparent from the data, the calcium boride is an acceptable termite toxicant, giving good 100% mortality, while at the same time, having an acceptable number of days to the first termite death.

EXAMPLE 4

The procedure of EXAMPLE 1 is repeated, with the exception that the termites are exposed to a bait containing 10% ulexite for a variable period of days, ranging from one day to four days. After the appropriate exposure period, the bait is removed and the termites are observed to the number of days to 100% mortality. The test was replicated three times with each test containing 20 termites. The averages to 100% mortality are 17.3 for one day's exposure, 19.3 for two day's exposure, 17.0 for three day's exposure and 15.0 for four day's exposure. This data shows that a relatively short exposure, i.e., one day, is sufficient to provide the same toxicity that a longer term exposure, such as that used in EXAMPLE 1. This is important since the termites need only visit the bait for a relatively short period of time to injest a lethal dosage.

EXAMPLE 5

The procedure of EXAMPLE 4 is repeated, with the exception that colemanite is used in place of the ulexite. The results of this testing are one day, 23.3; two days, 21.6; three days, 21.0; and four days 18.1. Again, this shows little reduction in activity with a short exposure to the bait containing the toxicant.

EXAMPLE 6

The procedure of EXAMPLE 4 was repeated, with the exception that the calcium boride was used in place of the ulexite. The termites were exposed from one to seven days. The results of the three replicates are as follows: one day, 30.3 days; two days, 17.3 days; three days, 13.7 days; four days, 13.3 days; five days, 12.3 days; six days, 10.7 days; and seven days, 10.0 days. Although the average days to 100% mortality decreases with a longer exposure, again, a relatively short exposure, i.e., one day, is sufficient to enable the termites to injest a lethal dosage.

EXAMPLE 7

The bait prepared in EXAMPLE 1 was then tested in a feeding preference test. In this test, one petri dish contained only a bait containing 10% ulexite, a second petri dish had bait without the toxicant as a control, and a third dish had both types. The average number of days to the first death for five replicates was 4.4 where the termites were given no choice, while the average was 5.0 where the termites were given a choice between a bait containing a toxicant and one not containing a toxicant. This indicates that termites will feed as readily on baits with a toxicant as well as the untreated baits. Furthermore, the average number of days to 100% mortality is essentially similar.

EXAMPLE 8

The procedure of EXAMPLE 7 is repeated, except that the ulexite is replaced with colemanite. In this case, the average number of days where there was no choice is 4.4; while the average number of days where there is a choice is 5.0. As these numbers are fairly close, it indicates that the termites will feed as readily on baits containing colemanite as on baits not containing any toxicant. Furthermore, the number of days to 100% mortality is similar.

EXAMPLE 9

The procedure of EXAMPLE 7 is repeated, with the exception that calcium boride was used as the toxicant, and that only three replicates were conducted. The average number of days to first death is 5.0 where there was no choice, and it is 5.7 were a choice is provided. The average number of days to 100% mortality is 13.7 where there is no choice and 14.7 where there is a choice. This clearly shows that the termites will feed as readily upon baits containing the calcium boride as baits not containing any toxicant.

I claim:

1. A termite bait composition, comprising an effective amount of wood innoculated with brown rot, fungus, *lenzites trabea,* and from 0.1 to 20% by weight of a boron containing toxicant selected from the group consisting of ulexite, colemanite, calcium boride and mixtures thereof.

2. The composition of claim 1 wherein the calcium boride is ulexite.

3. The composition of claim 1 wherein the boron compound is present in an amount of from 0.5 to 10% by weight.

4. The composition of claim 1 wherein the composition includes a substantial amount of a cellulosic binder.

5. The composition of claim 1 wherein the boron compound is present in an amount of from 1 to 5% by weight.

6. A method of protecting a structure from termites comprising placing an effective amount of a bait composition, an effective amount of wood innoculated with brown rot fungus, *lenzites trabea,* and from 0.1 to 20% by weight of a boron containing toxicant selected from the group consisting of ulexite, colemanite, calcium boride and mixtures thereof around said structure.

7. The method of claim 6 wherein the calcium boride is ulexite.

8. The method of claim 6 wherein the boron compound is present in an amount of from 0.5 to 10% by weight.

9. The method of claim 6 wherein the composition includes a substantial amount of a cellulosic binder.

10. The method of claim 6 wherein the boron compound is present in an amount of from 1 to 5% by weight.

* * * * *